(12) United States Patent
Kim et al.

(10) Patent No.: US 9,228,925 B2
(45) Date of Patent: Jan. 5, 2016

(54) AUTOMATED VITRIFICATION DEVICE

(75) Inventors: S. Samuel Kim, Mission, KS (US);
Sarah L. Kieweg, Lawrence, KS (US);
Todd McDonald, Lenexa, KS (US)

(73) Assignee: University of Kansas, Lawrence, KS (US)

( * ) Notice: Subject to any disclaimer, the term of this patent is extended or adjusted under 35 U.S.C. 154(b) by 100 days.

(21) Appl. No.: 14/236,418

(22) PCT Filed: Aug. 3, 2012

(86) PCT No.: PCT/US2012/049482
§ 371 (c)(1),
(2), (4) Date: Jun. 10, 2014

(87) PCT Pub. No.: WO2013/020032
PCT Pub. Date: Feb. 7, 2013

(65) Prior Publication Data
US 2014/0335555 A1 Nov. 13, 2014

Related U.S. Application Data

(60) Provisional application No. 61/515,149, filed on Aug. 4, 2011.

(51) Int. Cl.
*A61B 10/00* (2006.01)
*G01N 1/42* (2006.01)
*A01N 1/02* (2006.01)

(52) U.S. Cl.
CPC ............... *G01N 1/42* (2013.01); *A01N 1/0242* (2013.01); *A01N 1/0252* (2013.01); *A01N 1/0268* (2013.01)

(58) Field of Classification Search
CPC ............................. G01N 1/42; A01N 1/0242
See application file for complete search history.

(56) References Cited

U.S. PATENT DOCUMENTS

| | | |
|---|---|---|
| 2002/0115054 A1 | 8/2002 | Forest et al. |
| 2009/0120106 A1 | 5/2009 | Chin |
| 2009/0123992 A1 | 5/2009 | Chin |
| 2009/0123996 A1 | 5/2009 | Chin |
| 2009/0186405 A1 | 7/2009 | Chin |
| 2010/0317108 A1 | 12/2010 | Stojanov |
| 2012/0251999 A1 | 10/2012 | Demirci et al. |

FOREIGN PATENT DOCUMENTS

| | | |
|---|---|---|
| WO | WO 02/080670 | 10/2002 |
| WO | WO 2009/018521 | 2/2009 |

(Continued)

OTHER PUBLICATIONS

McDonald, "Design of Vitrification Machine," Thesis, University of Kansas, Mechanical Engineering, Available Jan. 3, 2011.

(Continued)

*Primary Examiner* — Jyoti Nagpaul
(74) *Attorney, Agent, or Firm* — Fanelli Haag PLLC

(57) ABSTRACT

The present application relates to devices for the vitrification of biological samples, including embryos, oocytes and biological tissues. Suitably, the devices are automated devices which require little if any operator intervention or sample handling, thereby reducing contamination, improving success rates and increasing efficiency. Also provided are methods of vitrifying a biological sample, suitably using the disclosed devices.

18 Claims, 16 Drawing Sheets

(56) References Cited

FOREIGN PATENT DOCUMENTS

| WO | WO 2010/011766 A1 | 1/2010 |
| WO | WO 2010/129569 A1 | 11/2010 |

OTHER PUBLICATIONS

Abdelhafez et al., "Vitrification in Open and Closed Carriers at Difference Cell Stages: Assessment of Embryo Survival, Development, DNA Integrity and Stability during Vapor Phase Storage for Transport," BMC Biotechnology, Mar. 2011, 11:29, pp. 1-10.

Isachenko et al., "Human ovarian tissue vitrification versus conventional freezing: morphological, endocrinological, and molecular biological evaluation," Reproduction, vol. 138 No. 2, Aug. 2009, pp. 319-327.

FEI Company, "Vitrobot Mark IV, Cool Science," FEI Company, Tools for Nanotech, product brochure, Jul. 2007.

FEI Company, "Vitrobot Mark IV," FEI Company, Product data, Feb. 2009.

International Search Report issued in International Application No. PCT/US12/049482 on Feb. 15, 2013.

Partial Supplementary European Search Report issued in European Application No. 12820685.1 on May 29, 2015.

AUTOMATED VITRIFICATION DEVICE

This application is a National Stage application of PCT/US2012/049842, filed Aug. 3, 2012, which claims the benefit of U.S. Provisional Patent Application No. 61/515,149, filed Aug. 4, 2011, the disclosures of each of which are incorporated herein by reference in their entireties.

BACKGROUND OF THE INVENTION

1. Field of the Invention

The present application relates to devices for the vitrification of biological samples, including embryos, oocytes and biological tissues. Suitably, the devices are automated devices which require little if any operator intervention or sample handling, thereby reducing contamination, improving success rates and increasing efficiency. Also provided are methods of vitrifying a biological sample, suitably using the disclosed devices.

2. Background of the Invention

Freezing and preservation of biological samples had traditionally been carried out using a slow-freezing process. Those methods were accomplished by tabletop machines that slowly cooled a sample over the period of several hours to cryogenic temperatures. These "slow freezing methods" have recently being supplanted by sample "vitrification," which allows for rapid freezing and storing of specimens in a matter of minutes instead of hours.

However, current vitrification devices require significant operation by a skilled lab technician. Success rates of vitrification and warming viable samples vary widely depending on the method used and the skill of the lab technician performing the procedure. Such methods traditionally require a lab technician to prepare individual samples for freezing, handle each separately and carry out specified methods. These methods, however, are not only time-consuming and inefficient, but can result in variations in sample vitrification due to differences in technician training and technique. This makes it extremely difficult to evaluate and compare various protocols. In addition, many manual vitrification methods expose the specimen directly to liquid nitrogen (i.e., open system), which provides rapid cooling (vitrification), but can lead to introduction of contaminants (fungi, pathogens etc.) to the specimen, as well as sample loss and damage.

The inventors have identified a need for protocols and devices that can be used to repeatedly and efficiently vitrify biological samples, including for use in fertility preservation and tissue banking.

SUMMARY OF PREFERRED EMBODIMENTS

The present application provides automated vitrification devices, as well as methods of vitrification that meet the needs identified above.

In embodiments, automated vitrification devices are provided. Suitably, such devices comprise a cryo-protectant holder, a cryo-protectant dispenser, a sample holder oriented to allow a sample in the sample holder to be contacted with cryo-protectant from the cryo-protectant dispenser, a sample sealing device, a coolant holder oriented to allow a sealed sample to be placed in a coolant in the coolant holder, and a control module operably connected to the cryo-protectant dispenser, the sample holder and the sample sealing device.

Suitably, the cryo-protectant dispenser is operably connected to a driving mechanism that controls the movement of the cryo-protectant dispenser. In embodiments, the various components of the devices are housed within a chamber, the chamber comprising at least one opening for introduction of the sample to the sample holder.

In embodiments, the sample holder is a rotating sample holder that moves the sample from a position that allows introduction of the sample, to a position that allows introduction of the cryo-protectant from the cryo-protectant dispenser. Suitably, the rotating sample holder further moves the sample from the position that allows introduction of the cryo-protectant to a position that allows sealing of the sample by the sample sealing device.

In embodiments, the devices further comprise a drying mechanism for removing excess cryo-protectant from the sample. Suitably, the sample sealing device comprises a sealing mechanism and a cutting mechanism for first sealing the sample, then cutting the sealed sample, and then releasing the sealed sample from the sample holder into the coolant holder. Suitably, the coolant in the coolant holder is liquid nitrogen.

In embodiments, the sealing mechanism comprises an adhesive film and the cutting mechanism comprises a first die and a second that align together.

In further embodiments, automated vitrification devices are provided that comprise a cryo-protectant holder, a cryo-protectant dispenser, a sample holder oriented to allow a sample in the sample holder to be contacted with cryo-protectant from the cryo-protectant dispenser, a drying mechanism for removing excess cryo-protectant from the sample, a sample sealing device comprising a sealing mechanism and a cutting mechanism for first sealing the sample, then cutting the sealed sample. The devices also comprise a coolant holder oriented to allow the sealed sample to be placed in a coolant in the coolant holder and a control module operably connected to the cryo-protectant dispenser, the sample holder and the sample sealing device. Suitably, the various device components are housed within a chamber, the chamber comprising at least one opening for introduction of the sample to the sample holder.

Also provided are containers for a biological sample, comprising a support member having a top surface and a bottom surface, a sample retention area (e.g., a substantially circular hole) traversing the support member from the top surface to the bottom surface and a porous mesh positioned in the sample retention area. Suitably, the sample retention area allows for introduction of the biological sample onto the porous mesh and removal of a fluid from the porous mesh. Suitably, the sample retention area comprises an extension surrounding said hole, extending at least above said top surface of said support member. In embodiments, the containers further comprise a frame supporting the container.

Also provided are methods of vitrifying a biological sample. Such methods suitably comprise placing a biological sample in a sample holder, placing a cryo-protectant in a cryo-protectant holder, dispensing the cryo-protectant from the cryo-protectant holder onto the sample, removing excess cryo-protectant from the sample via a drying mechanism, sealing the sample, cutting the sealed sample, and transferring the sealed sample into a coolant in a coolant holder.

Suitably, the dispensing, removing, sealing, cutting and transferring are automated via a control module.

Further embodiments, features, and advantages of the embodiments, as well as the structure and operation of the various embodiments, are described in detail below with reference to accompanying drawings.

DETAILED DESCRIPTION OF PREFERRED EMBODIMENTS

It should be appreciated that the particular implementations shown and described herein are examples and are not intended to otherwise limit the scope of the application in any way.

The published patents, patent applications, websites, company names, and scientific literature referred to herein are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of ordinary skill in the art.

Figure 1:
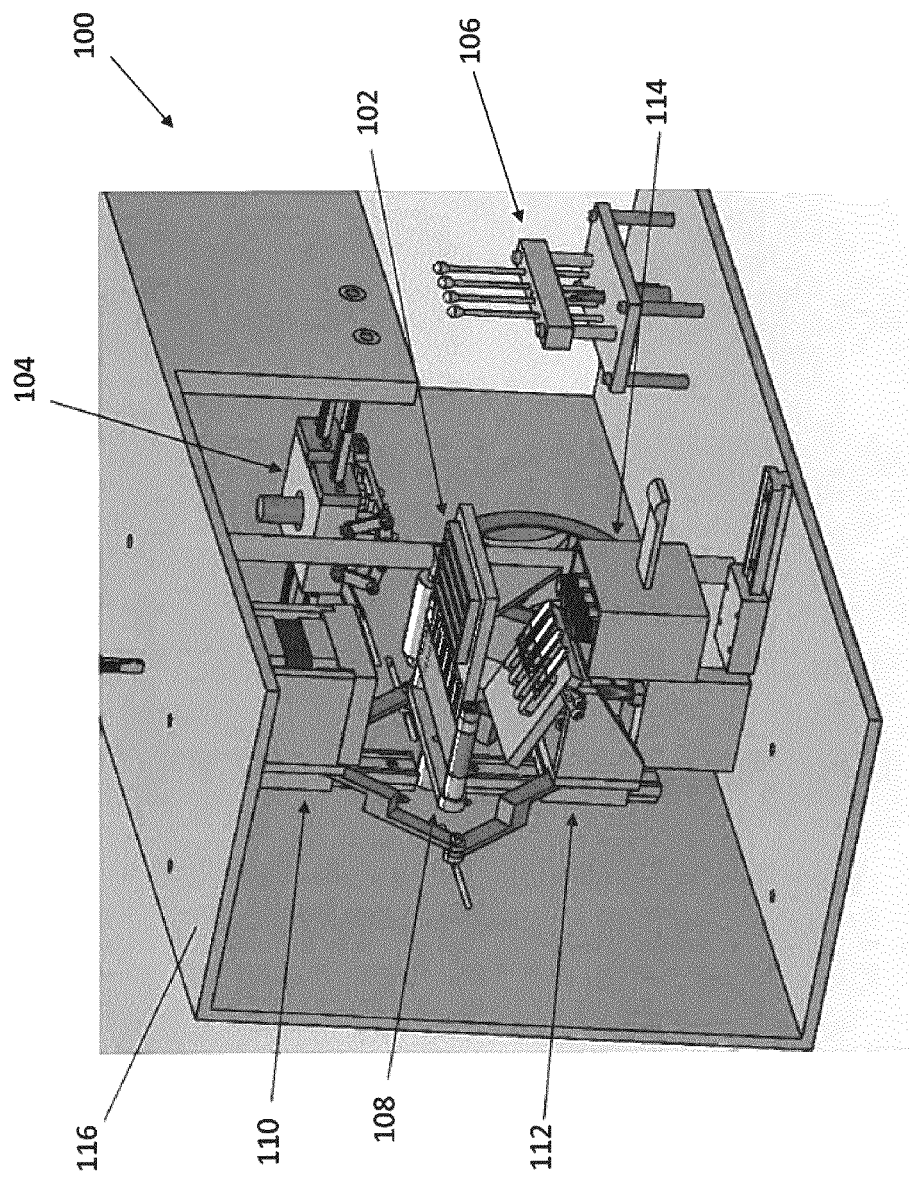
FIG. 1 shows an exemplary automated vitrification device as described herein.

In embodiments, an automated vitrification device 100, for example as shown in FIG. 1, is provided.

As used herein "automated" refers to a device that operates, i.e., proceeds step-by-step through various mechanical movements and actions, with little or no intervention or control from a human operator. In general, the automated devices described herein are controlled via computer or other suitable control module.

The term "vitrification" as used herein refers to the solidification of a liquid by an extreme elevation of viscosity as a result of the rapid cooling of a sample below about −110° C., suitably below about −150° C., to preserve the sample and allow it to be stored for extended periods, e.g., days, weeks, months, years, etc.

As shown in FIG. 1, automated vitrification device 100 suitably comprises cryo-protectant holder 102. In embodiments, cryo-protectant holder 102 comprises a base 204 that contains one or more reservoirs 206 suitable for receiving and holding a cryo-protectant. Base 204 suitably sits on a rotating platform 202, which rotates about rotation point 210. As used herein, "cryo-protectant" or "cryoprotectant" refers to a composition (suitably a fluid solution) that is used to protect biological samples from freezing damage due to ice crystal formation. Exemplary cryo-protectant solutions are known in the art, and include for example, solutions comprising ethylene glycol, dimethyl sulfoxide, propane-1,2-diol (PrOH), etc., and mixtures thereof. Suitably, base 204 comprises multiple (i.e., 2, 3, 4, 5, 6, 7, 8, 9, 10 or more) reservoirs 206 that can be used to hold different cryo-protectants. As described herein, it is often necessary during a vitrification procedure to contact a sample with more than one cryo-protectant (i.e., cryo-protectants having different compositions).

Cryo-protectant solutions for use in the devices and methods described herein suitably comprise ethylene glycol (EG), dimethyl sulfoxide (DMSO), sucrose and/or trehalose, and serum substitute supplement (SSS™) in modified human tubal fluid (mHTF) (suitably from Irvine Scientific, Santa Ana, Calif.). An exemplary cryo-protectant solution suitably comprises about 2% to about 30% EG, about 2% to about 20% DMSO, about 0.05 to about 1.0 M sucrose and/or about 0.05 to about 1.0 M trehalose, and about 5% to about 30% SSS™ in mHTF. More suitably, exemplary cryo-protectants comprise about 5% to about 20% EG, about 5% to about 10% DMSO, about 0.1 to about 0.5 M sucrose and/or about 0.1 to about 0.5 M trehalose, and about 15% to about 25% SSS in mHTF.

Exemplary cryo-protectant solutions comprise 1) about 7.5% EG, about 7.5% DMSO, about 0.1 M sucrose and about 20% SSS in mHTF; 2) about 10% EG, about 10% DMSO, about 0.3 M sucrose and about 20% SSS in mHTF; or 3) about 20% EG, about 10% DMSO, about 0.5 M sucrose, about 0.5 M trehalose, and about 20% SSS in mHTF. In embodiments, such cryo-protectant solutions are suitably used for vitrification of oocytes.

Additional exemplary cryo-protectant solutions comprise 1) about 7.5% EG, about 7.5% DMSO, about 0.1 M sucrose, and about 20% SSS in mHTF; 2) about 10% EG, about 10% DMSO, about 0.3 M sucrose, about 20% SSS in mHTF; or 3) about 20% EG, about 10% DMSO, about 0.5 M sucrose, about 0.5 M trehalose and about 20% SSS in mHTF. In embodiments, such cryo-protectant solutions are suitably used for vitrification of blastocysts.

As used herein, "biological material" and "biological sample" are used interchangeably and include material obtained from a human, plant or animal source, and includes for example, tissues, blood, cells, bone, oocytes, embryos, sperm, eggs, ovarian tissue, gamete, gonadal tissue, testicular tissue, etc.

Vitrification device 100 also suitably comprises cryoprotectant dispenser 104 as shown in FIG. 1. Cryo-protectant dispenser 104 is suitably oriented above cryo-protectant holder 102, as shown in FIG. 3, however in other embodiments, cryo-protectant dispenser 104 can be located below cryo-protectant holder 102, or can be in any other suitable orientation.

Cryo-protectant dispenser 104 suitably is operably connected to driving mechanism 302 that controls its movement in any suitable direction, (i.e., in any x, y or z direction, or combination of these directions) so as to remove (e.g., suction) cryo-protectant from cryo-protectant holder 102 via nozzles 304 or other suitable mechanism.

Figure 2:
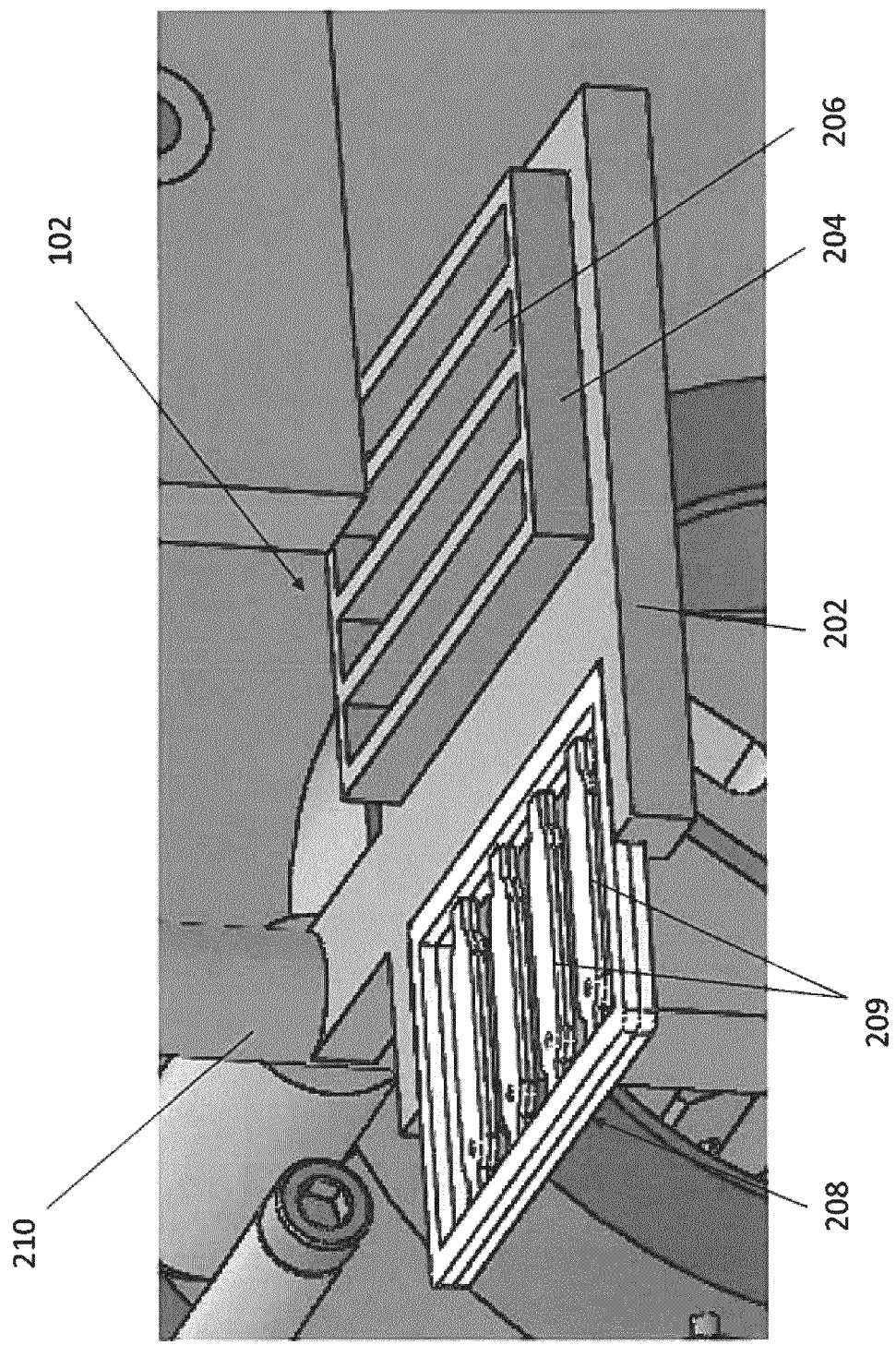
FIG. 2 shows a cryo-protectant holder and sample holder of an exemplary automated vitrification device as described herein.
Figure 3:
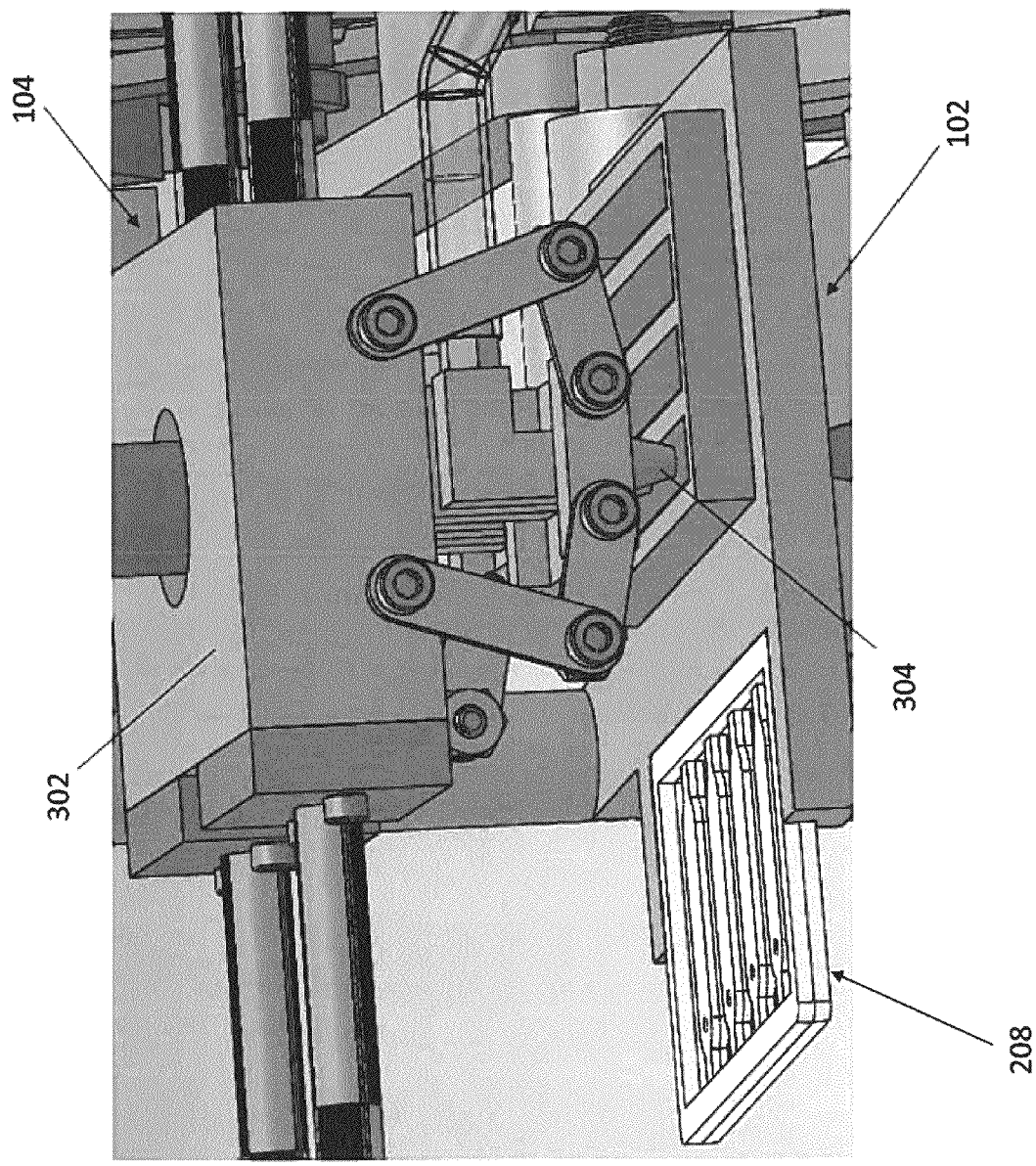
FIG. 3 shows a cryo-protectant dispenser, a cryo-protectant holder and sample holder of an exemplary automated vitrification device as described herein.

Automated vitrification device 100 also comprises sample holder 208, shown in FIG. 2 and FIG. 3. Sample holder 208 is suitably oriented so as to allow a sample in the sample holder to be contacted with one or more cryo-protectants from cryo-protectant dispenser 104. For example, cryo-protectant that is removed from reservoirs 206 via nozzles 304 can be administered/delivered to the sample in sample holder 208. Cryo-protectant dispenser 104 is able to control the amount of cryo-protectant administered to the sample and can administer multiple cryo-protectants to a single sample in any order, at any time, for any duration and in any amount desired by the operator via a control module as described herein.

For example, in embodiments, cryo-protectant dispenser administers cryo-protectants to a biological sample in the amounts and for the durations indicated below. Drying mechanism 106 is suitably used to remove excess cryo-protectant at the desired times/intervals prior to application of the next cryo-protectant.

Described below is an exemplary cryo-protectant protocol for vitrification of oocytes:
A solution comprising about 7.5% EG+about 7.5% DMSO+about 0.1 M sucrose+about 20% SSS in mHTF is applied to the biological sample for 5 minute;
Excess solution is removed;
A solution comprising about 10% EG+about 10% DMSO+ about 0.3 M sucrose+about 20% SSS in mHTF is applied to the biological sample for about 1 minute;
Excess solution is removed;
A solution comprising about 20% EG+about 10% DMSO+ about 0.5 M sucrose+about 0.5 M trehalose+about 20% SSS in mHTF is applied to the biological sample for about 40 seconds. This 40 second time suitably also includes sealing the sample prior to vitrification, as described herein.

Described below is an exemplary cryo-protectant protocol for vitrification of blastocysts:
A solution comprising about 7.5% EG+about 7.5% DMSO+about 0.1 M sucrose+about 20% SSS in mHTF is applied to the biological sample for about 10 minutes;
Excess solution is removed;
A solution comprising about 10% EG+about 10% DMSO+ about 0.3 M sucrose+about 20% SSS in mHTF is applied to the biological sample for about 1 minute;
Excess solution is removed;
A solution comprising about 20% EG+about 10% DMSO+ about 0.5 M sucrose+about 0.5 M trehalose+about 20% SSS in mHTF is applied to the biological sample for about 60 seconds. This 60 second time suitably also includes sealing the sample prior to vitrification, as described herein.

Figure 5:
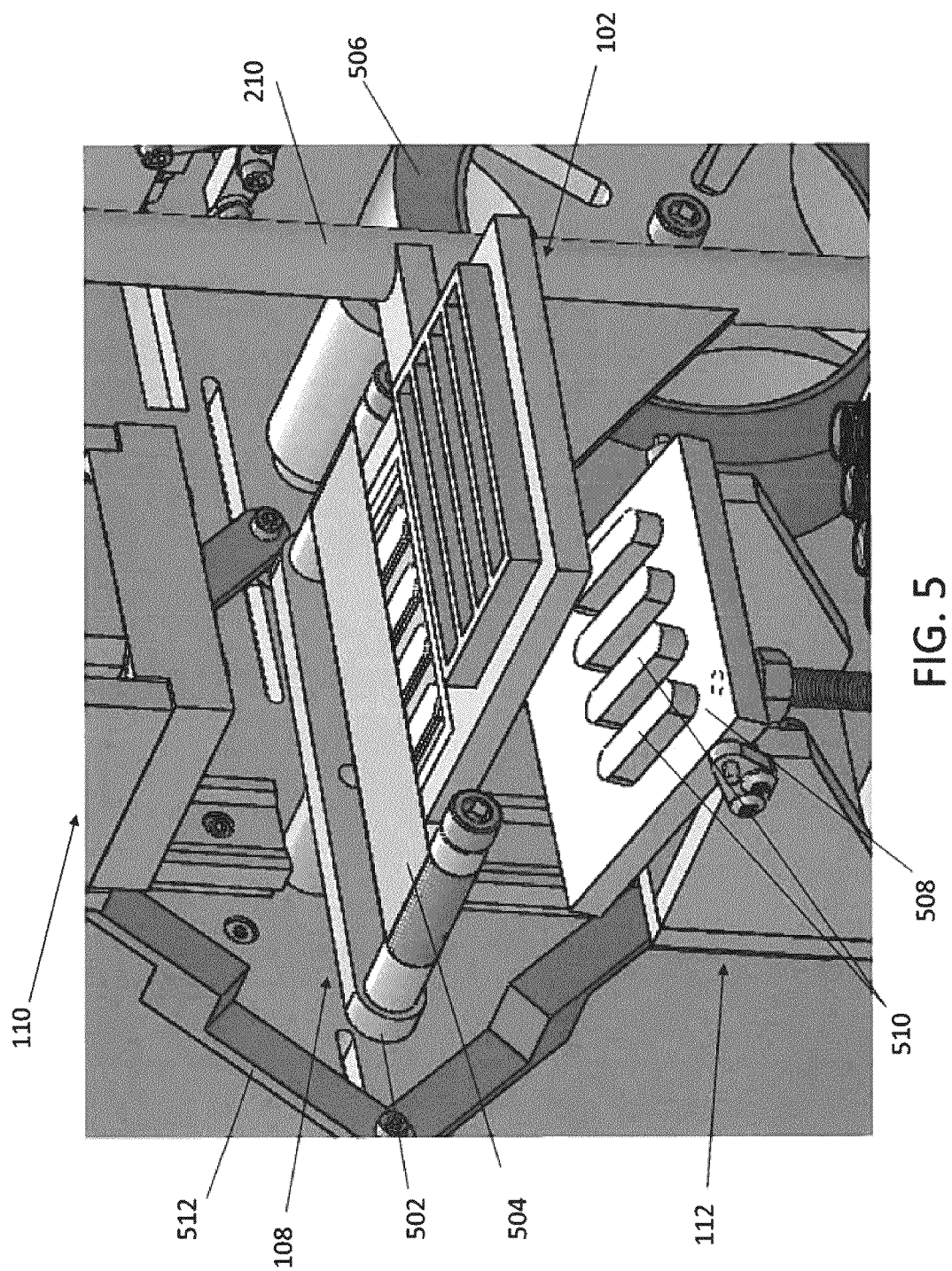
FIG. 5 shows a cryo-protectant holder, sample holder and sample sealing device of an exemplary automated vitrification device as described herein.
Figure 6:
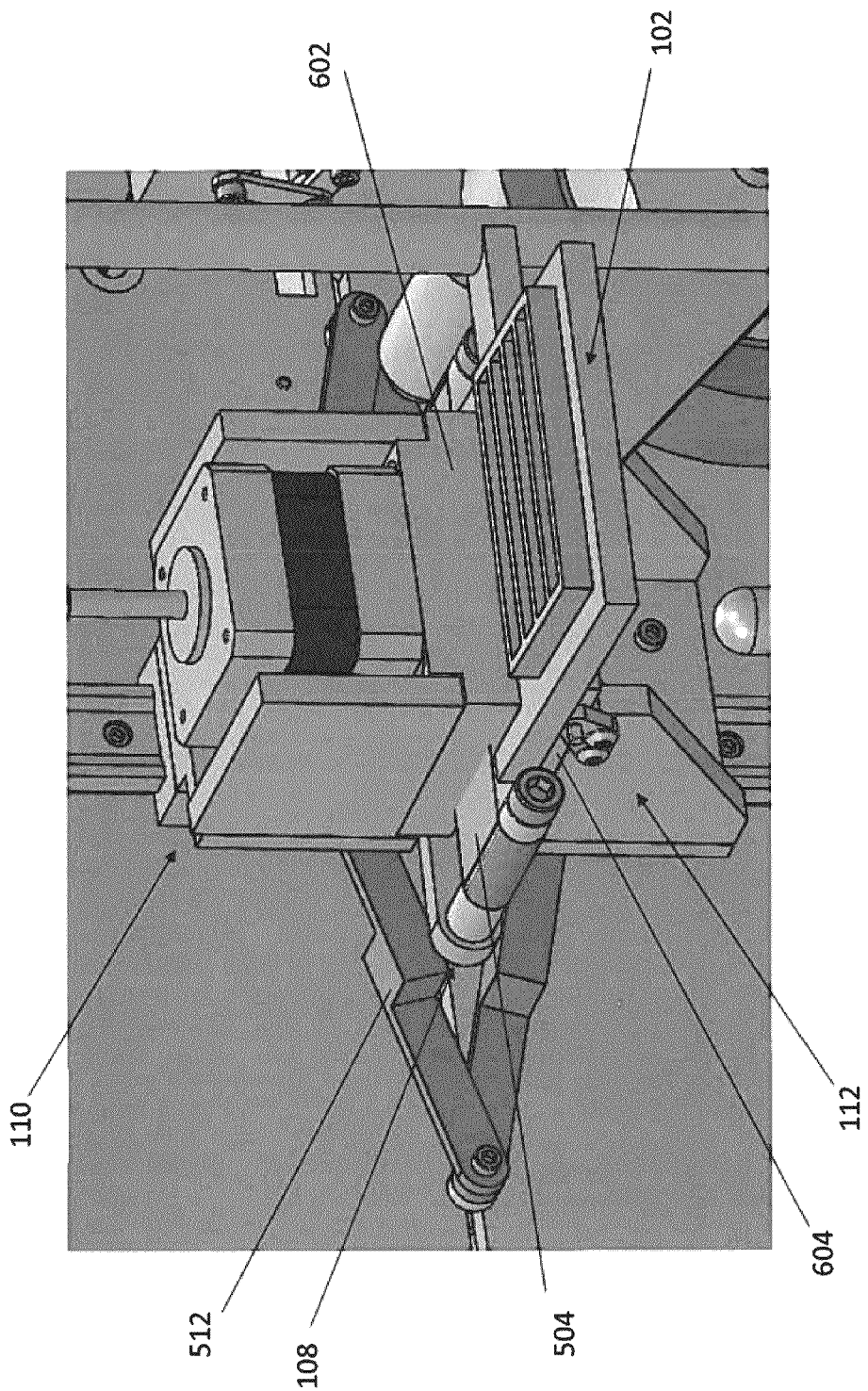
FIG. 6 shows and alternative view of a cryo-protectant holder, sample holder and sample sealing device of an exemplary automated vitrification device as described herein.

As shown in FIGS. 1, 5 and 6, automated vitrification device 100 suitably further comprises sample sealing device 110/108/112, having upper 110 and lower 112 sections. In embodiments, as shown in FIGS. 5 and 6, sample sealing device 110/108/112 suitably comprises a sealing mechanism 108 and a cutting mechanism (602 and 604).

Figure 8:
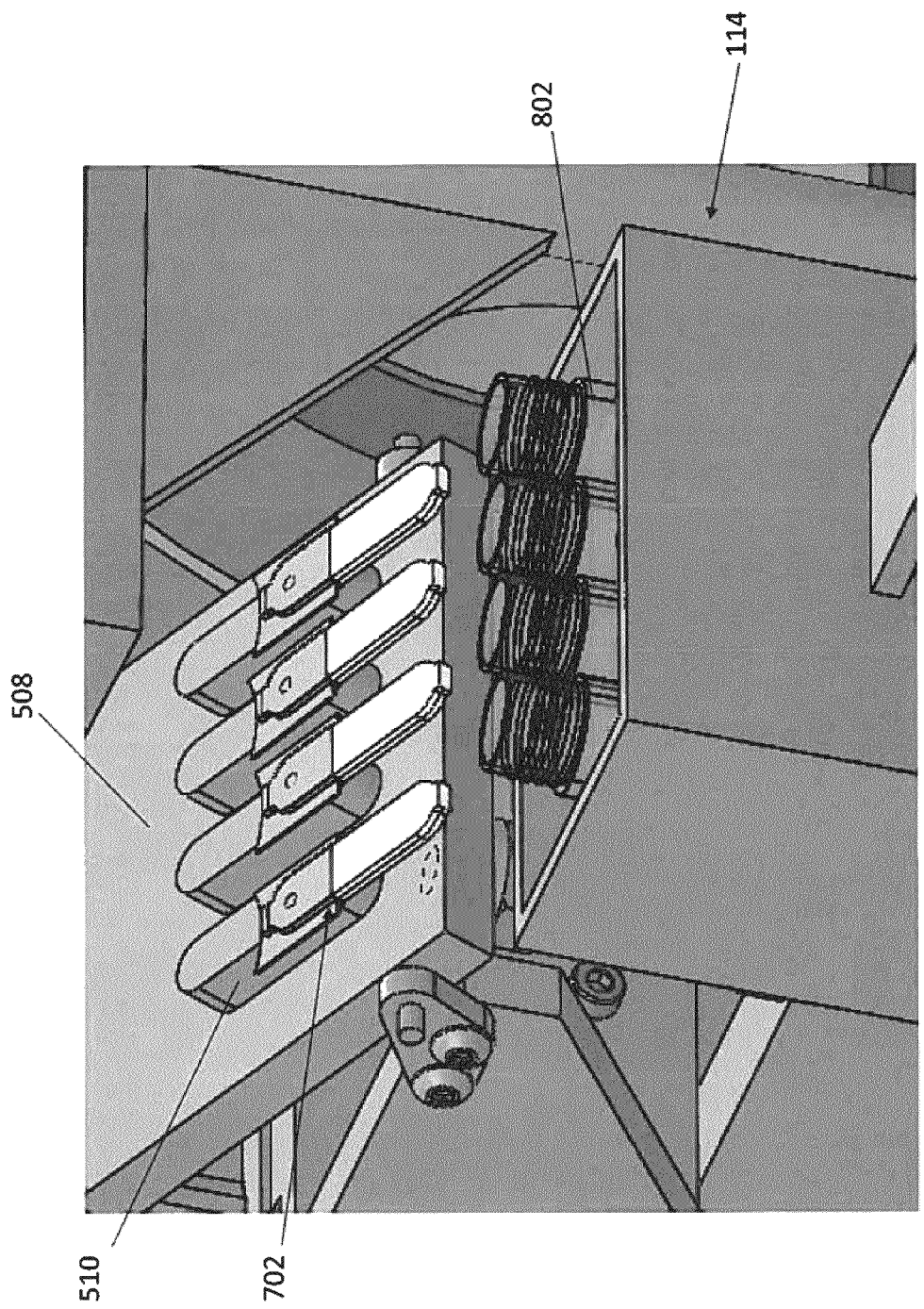
FIG. 8 shows a sealed sample and a coolant holder of an exemplary automated vitrification device as described herein.

Automated vitrification device 100 suitably also comprises coolant holder 114, as shown in FIG. 8. Suitably, coolant holder 114 is oriented to allow a sealed sample 702 to be placed in a coolant in the coolant holder.

As discussed herein, the automated vitrification devices described throughout are suitably under the control of a control module, suitably a computer or similar device, which is connected to one or more of the various components of the vitrification device so as to allow for automation of a vitrification process carried out by the device. Suitably, a control module (not shown) is operably connected to cryoprotectant dispenser 104, sample holder 208 and sample sealing device 110/108/112. In additional embodiments, a control module can be further connected to drying mechanism 106, cryo-protectant holder 102, as well as any other components.

Figure 12A:
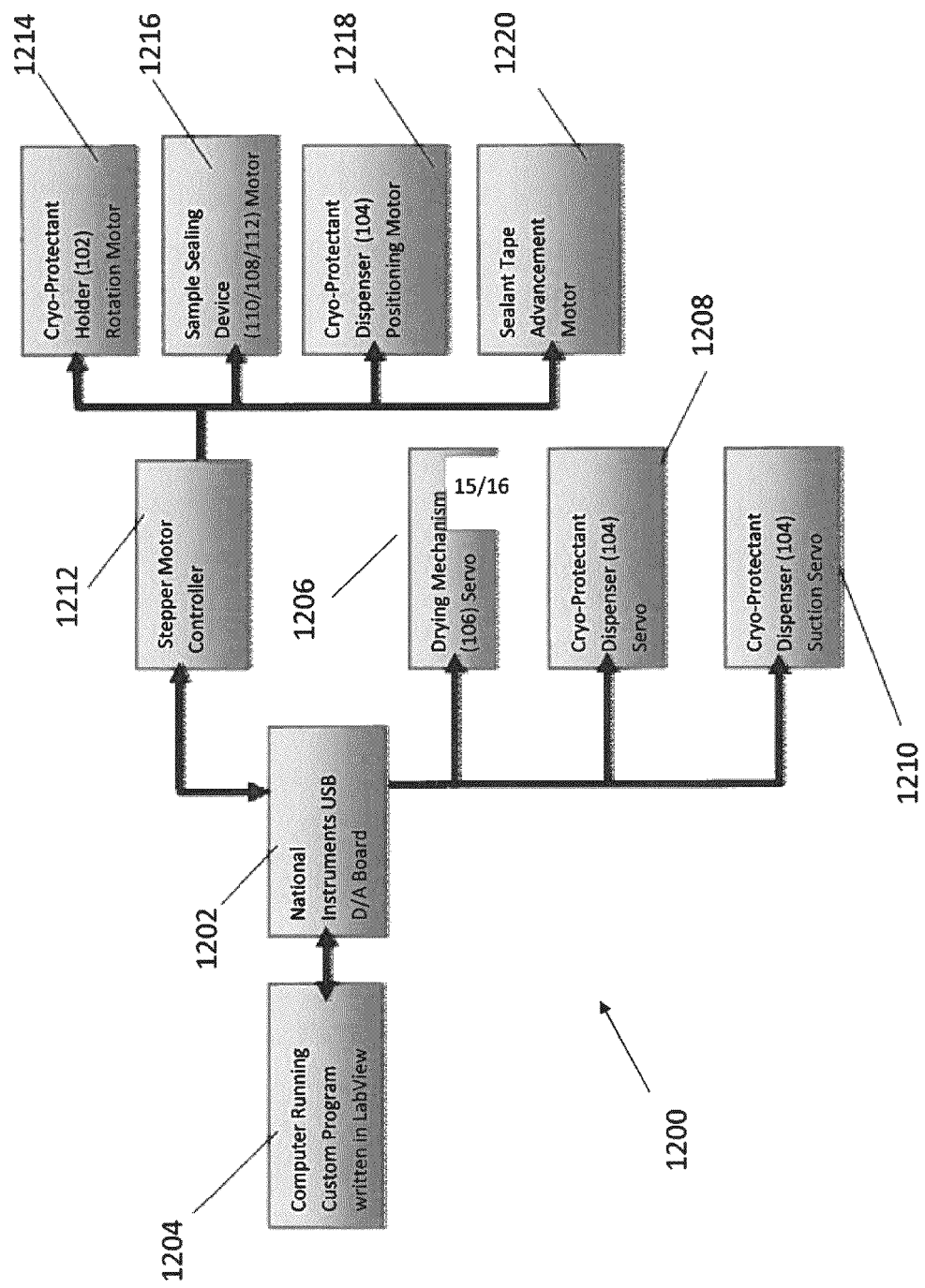
FIG. 12A shows an exemplary control system for use with an automated vitrification device as described herein.
Figure 12B:
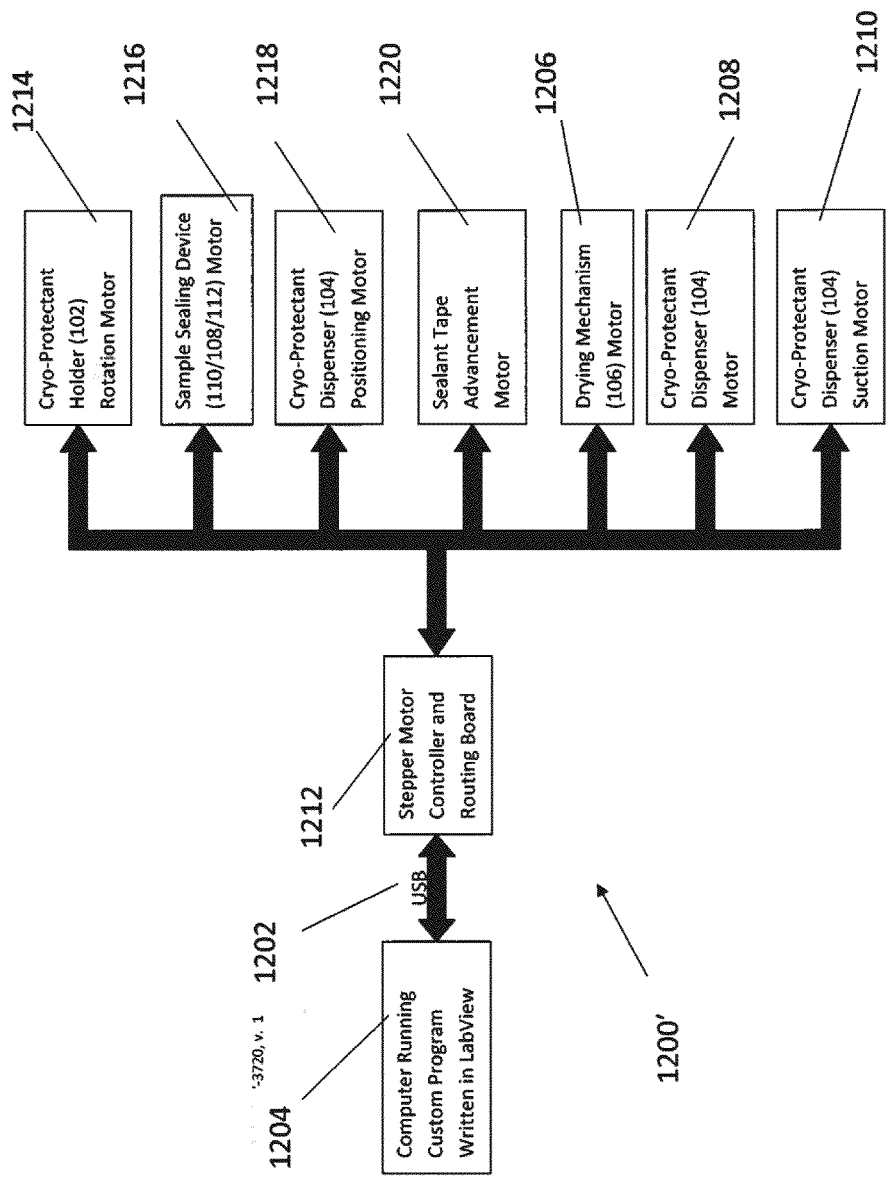
FIG. 12B shows an additional exemplary control system for use with an automated vitrification device as described herein.

FIG. 12A shows an exemplary control system 1200 for use with the automated vitrification devices described herein. In exemplary embodiments, control system 1200 comprises a National Instruments USB D/A Board 1202 running a custom program 1204 written in LabView. As shown in FIG. 12A, the D/A Board suitably controls three servos, including drying mechanism 106 servo 1206, cryo-protectant dispenser 104 servo 1208, and cryo-protectant dispenser suction (not shown) servo 1210 using pulse width modulation. The D/A Board is also connected stepper motor controller 1212 using a serial connection. Stepper motor controller 1212 suitably controls four stepper motors; cryo-protectant holder 102 rotation motor 1214, Sample Sealing Device 110/108/112 Motor 1216, Cryo-Protectant Dispenser 104 Positioning Motor 1218, and Sealant Tape Advancement (not shown) Motor 1220. FIG. 12B shows an additional exemplary control system 1200' for use with the automated vitrification devices described herein. Exemplary control system 1200' comprises components, including motors/servos, analogous to those disclosed in control system 1200.

In exemplary embodiments, the various components of automated vitrification device 100, as described herein, are housed within chamber 116, as shown in FIGS. 1, 9A, 9B and 9C. In embodiments, chamber 116 comprises at least one opening (not shown) that allows for introduction of a sample to sample holder 208. Suitably, chamber 116 is a metal enclosure that contains the various device components described herein.

As described herein, sample holder 208 is suitably a rotating sample holder attached to base 202 and connected to rotation point 210, which moves the sample from a position that allows introduction of the sample, to a position that allows introduction of the cryo-protectant from cryo-protectant dispenser 104. For example, as shown in FIG. 1, a sample is introduced into sample holder 208 in a first position. Sample holder 208 is then rotated to a position below cryo-protectant dispenser 104, in which cryo-protectant dispenser 104 is also able to remove cryo-protectant from reservoirs 206 of cryo-protectant holder 102 (see e.g., FIGS. 1, 2 and 3) and then administer the cryo-protectant to the samples.

Suitably, cryo-protectant dispenser 104 utilizes a stepper motor to drive two ACME screws that move the main exposure carriage (e.g., 302). The dispenser suitably uses a six-bar linkage driven by a linear solenoid to retrieve cryo-protectant from the reservoirs and place them on the samples. Each nozzle (suitably 2, 3, 4, 5, 6, 7, 8, 9 10, etc. nozzles) is independently controlled by its own solenoid, which draws the cryo-protectant into the nozzles and pushes them out using a suitable device, such as a syringe.

The rotating sample holder is further able to move the sample from the position where the cryo-protectant is introduced, to a position that allows sealing of the sample by sample sealing device 110/108/112, as in FIG. 5. As shown in FIGS. 5 and 6, sample sealing device suitably comprises sealing mechanism 108. In exemplary embodiments, sealing mechanism 108 comprises an adhesive or other suitable film 504, for example an adhesive tape. As shown in FIG. 5, in embodiments, sealing mechanism 504 is wound over arms 502 that create an envelope or pocket into which sample holder 208 is inserted, as shown in FIG. 5. Sealing mechanism 504 in the form of adhesive tape can suitably be stored on storage roll 506 (or multiple storage rolls as shown in FIG. 9B) prior to use in sample sealing device 110/108/112. As shown in FIG. 5, sample holder 208 is rotated into position with sealing mechanism 504 via a rotation platform about rotation point 210.

Sample sealing device 110/108/112 suitably comprises a cutting mechanism for first sealing the sample (FIG. 5), then cutting the sealed sample (FIG. 6), and then releasing the sealed sample 702 from the sample holder into the coolant holder 114.

In exemplary embodiments, cutting mechanism comprises a first die 602 (i.e., an upper die 602 on upper portion 110 of sealing device 110/108/112) and a second die 604 (i.e., a lower die on lower portion 112 of sealing device 110/108/112) that align together, as shown in FIG. 6. It should be understood that orientation of upper and lower die are for illustration purposes, and any suitable orientation can be used. In addition, other mechanisms to cut and seal sample 208 can also be used. As shown in FIG. 6, first die 602 and second die 604 are brought into contact so as to seal and cut the sample via collapsing arms 512. A person of ordinary skill in the art will readily be able to envision other suitable mechanisms for sealing and cutting sample 208.

Sealing sample utilizing a sealing mechanism such as an adhesive film or tape provides a mechanism by which the sample can be vitrified, but without actually directly contacting the sample with liquid nitrogen, thereby reducing contamination and sample loss or damage.

Suitably, a stepper motor is used to drive the movement of the sealing device 110/108/112, and a slot-and-linkage arrangement is used to control the movement. The assembly has mating upper 602 and lower 604 dies that press the sealing mechanism, e.g., sealant tape, onto containers 208, cut the tape, punch out the containers from their handling frame and tilt to put the containers into coolant, as described herein.

The sealing tape is placed in the machine on a roll 506 (or multiple rolls as shown in FIG. 9B) and is tensioned by a spring-loaded roller and arm 502 (or multiple arms as shown in FIG. 9B). The tape attaches to a roller, which is driven by a stepper motor to pull the sealing tape into an envelope-type arrangement. The specimens are then rotated into the envelope where they are sealed, punched out and vitrified.

Figure 7:
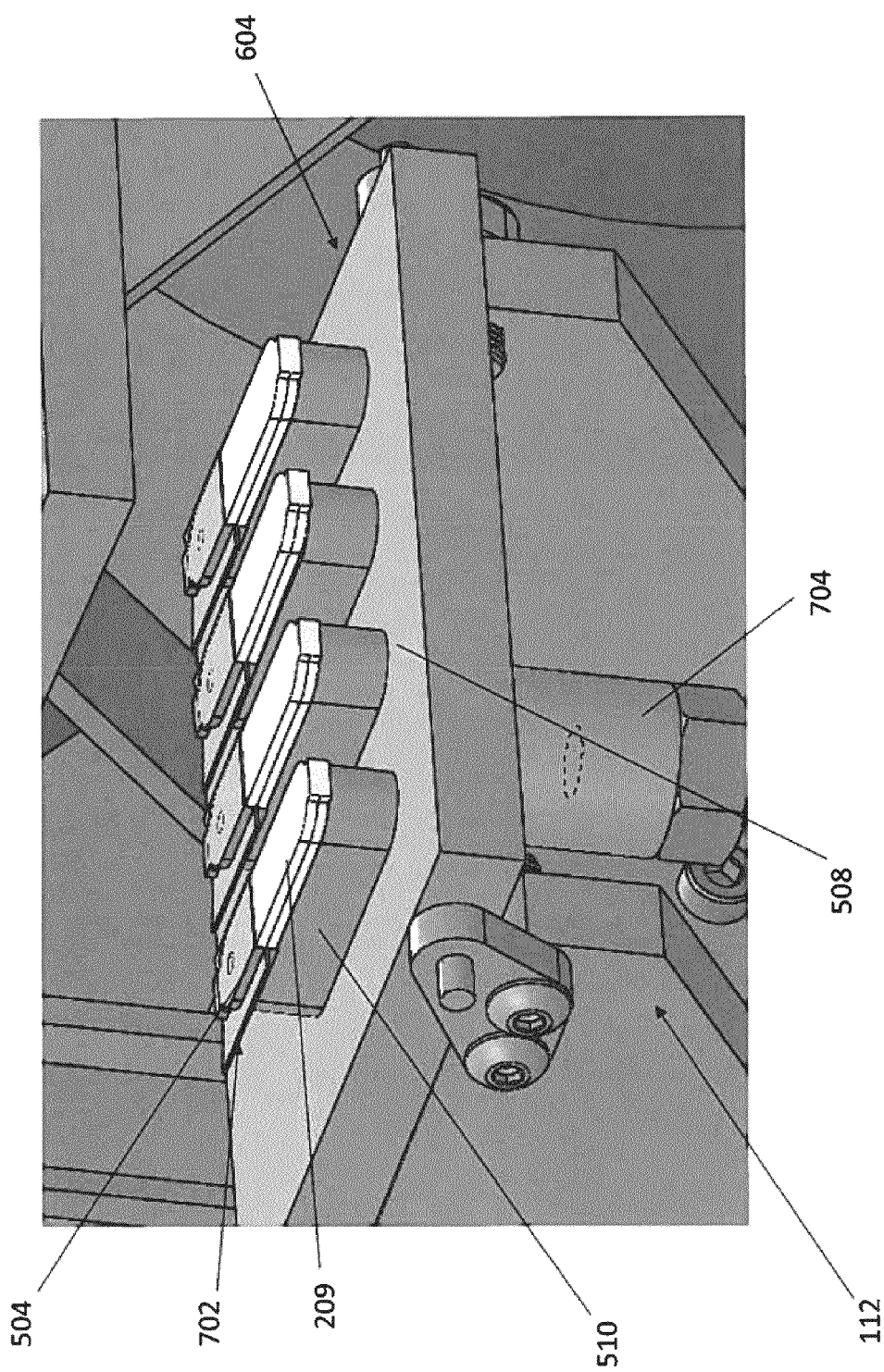
FIG. 7 shows a sealed sample of an exemplary automated vitrification device as described herein.

FIG. 7 shows a sealed sample 702, comprising sealing mechanism 504 covering and securing sample 208, as well as individual separated support members 209 of the sample holder 208. The lower portion 112 of sealing device 110/108/112 suitably comprises raised portions 510 on platform 508 of second die 604, see FIGS. 5 and 7.

As lower die 604 is lowered, it contacts rod 704, which causes the die to tilt, thereby releasing the sealed sample 702 into the coolant holder 114. Suitably, coolant holder 114 comprises individual cryo-vials 802, each individually containing a coolant, suitable for receiving the sealed samples. In exemplary embodiments, the coolant is liquid nitrogen. Other suitable coolants include, for example, liquid helium, etc.

Figure 4:
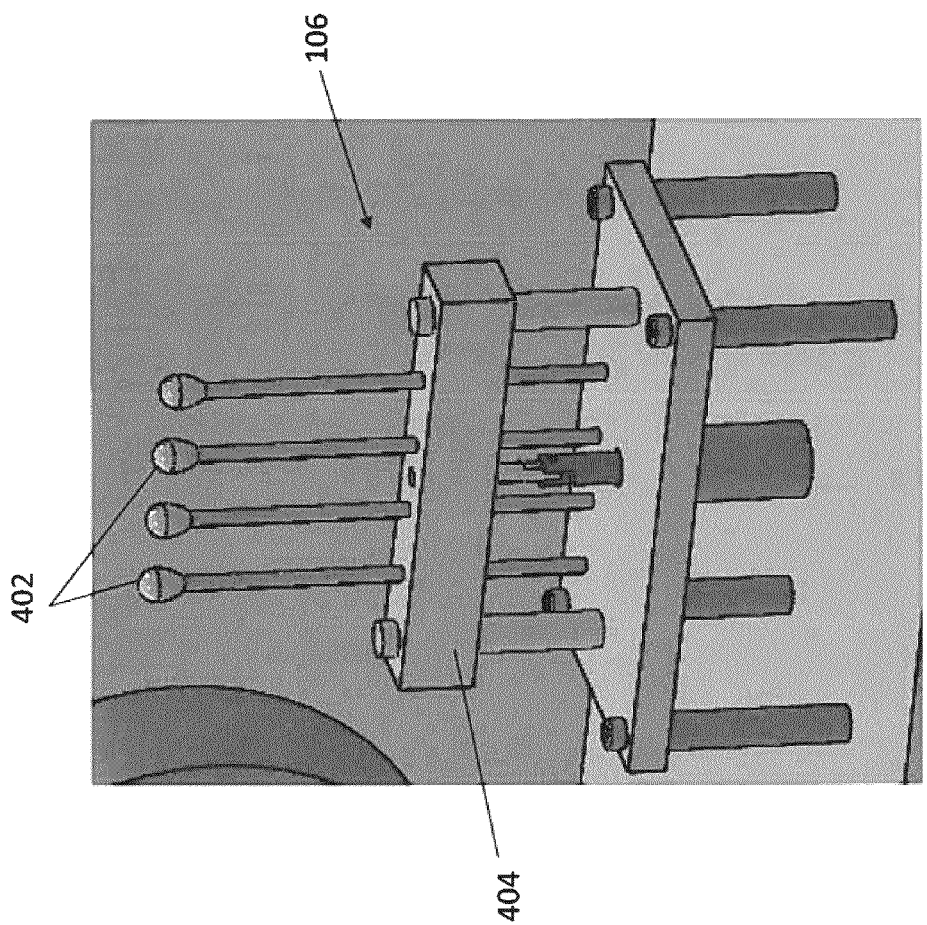
FIG. 4 shows a drying mechanism of an exemplary automated vitrification device as described herein.

As shown in FIGS. 1 and 4, the automated vitrification device 100 suitably further comprises a drying mechanism 106, for removing excess cryo-protectant from the sample. Drying mechanism 106 suitably comprises multiple (i.e., 2 or more, 3, 4, 5, 6, 7, 8, 9, 10 or more) individual drying elements 402 (suitably a cloth or cotton swab or other suitable adsorbent material) positioned in a base 404. As shown in FIG. 1, following the addition of cryo-protectant to the sample 208 with cryo-protectant dispenser 104, the sample is rotated about rotation point 210, so that the samples are directly above drying elements 402. It should be noted that this orientation is for illustrative purposes only, and in other embodiments, the drying mechanism 106 can be positioned above the sample holder, or any other suitable orientation can be used.

Drying mechanism 106 is used to remove excess cryoprotectant (surplus cryo-protectant that is not necessary for the vitrification as well as cryo-protectant that may interfere with additional cryoprotectants) prior to introduction of a subsequent cryo-protectant to the sample. As described herein, vitrification methods suitably utilize multiple different cryo-protectants, each or which requires contact with a sample for a particular amount of time and in a particular order.

Figure 9A:
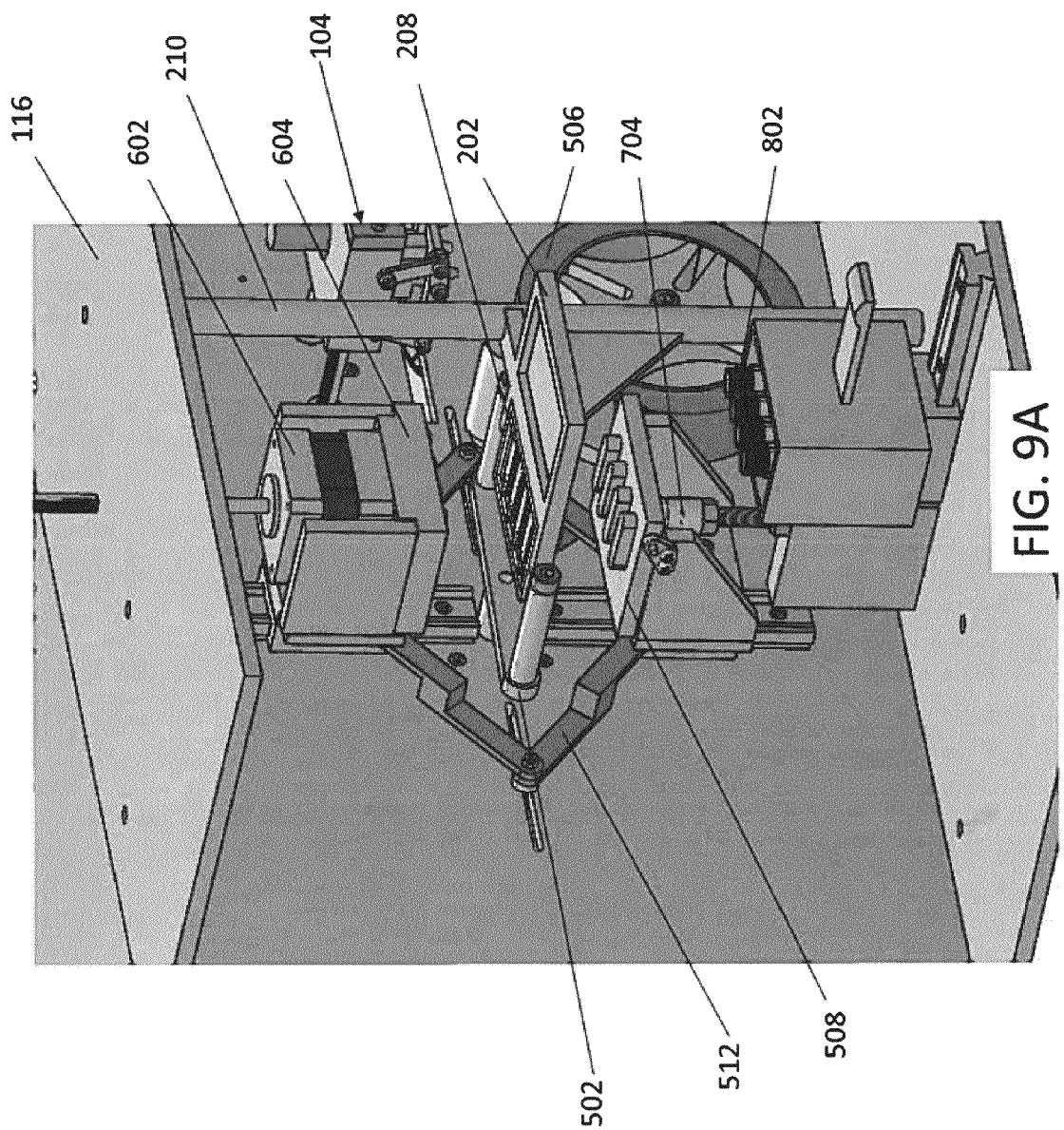
FIG. 9A shows an alternative view of an exemplary automated vitrification device as described herein.
Figure 9B:
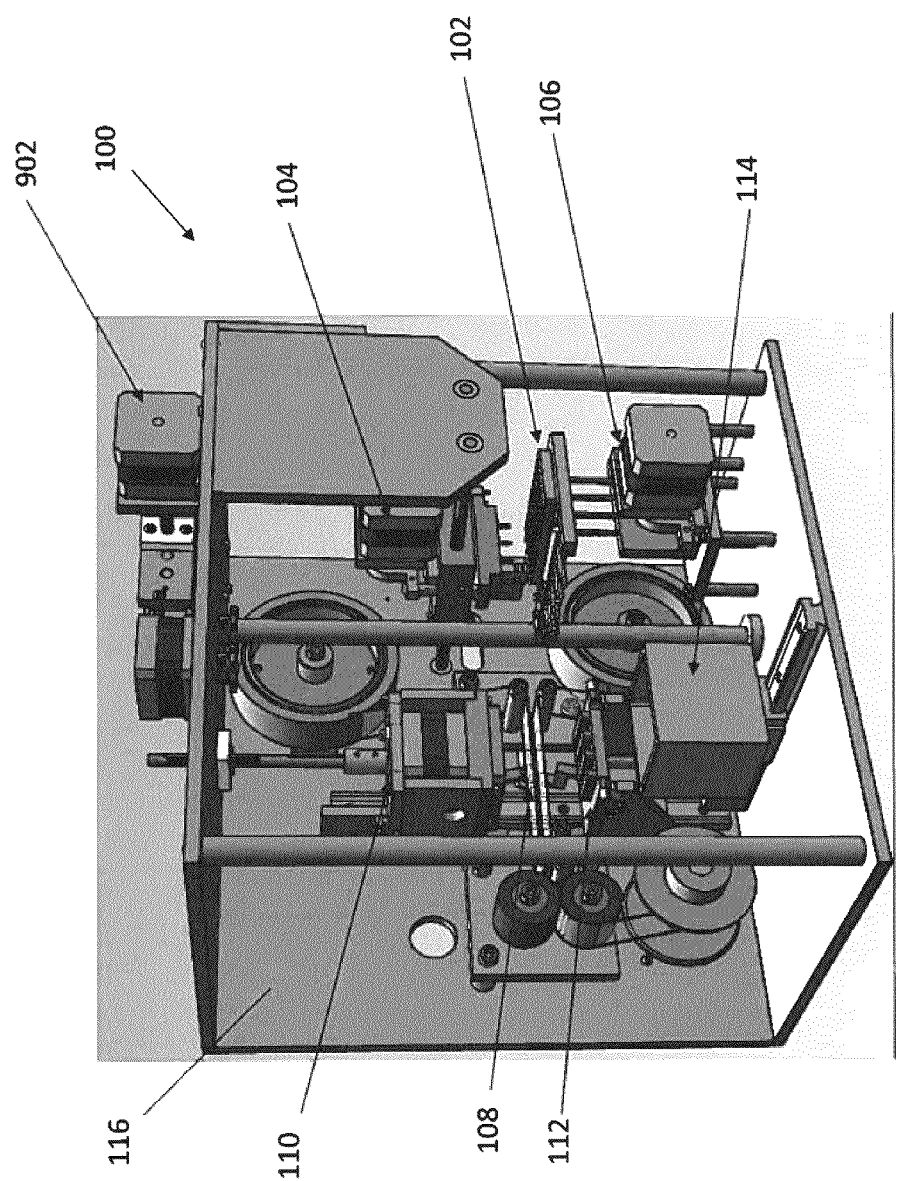
FIG. 9B shows an additional exemplary automated vitrification device as described herein.
Figure 9C:
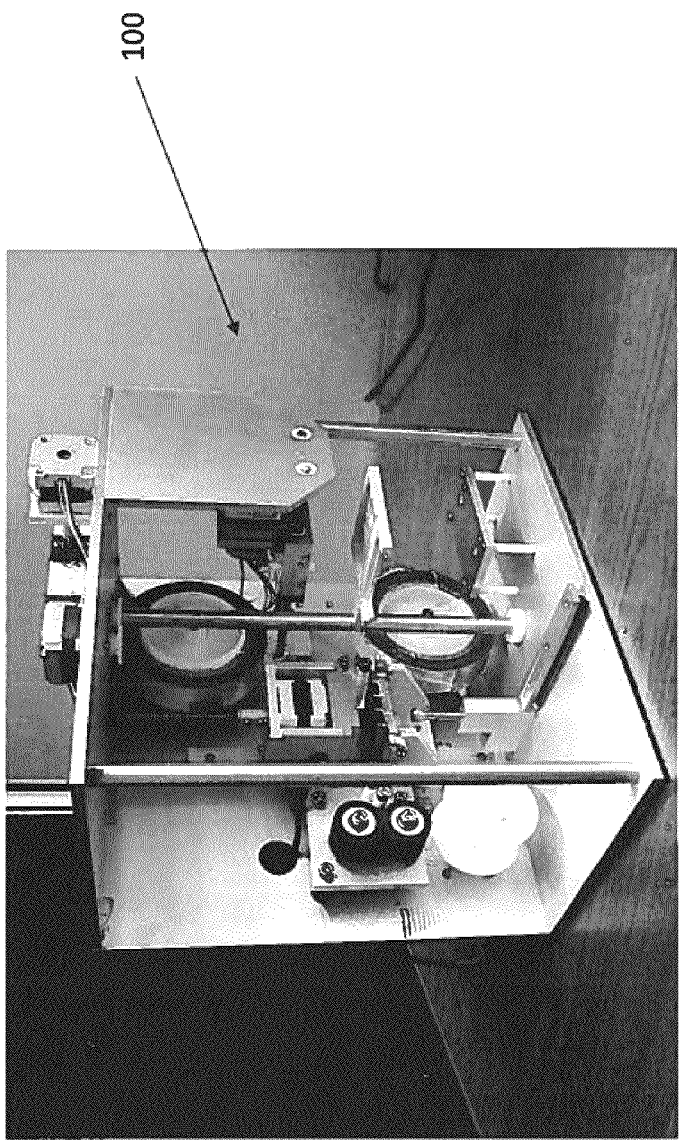
FIG. 9C shows an alternative view of an exemplary automated vitrification device as described herein.

FIG. 9A shows an additional view of an automated vitrification device as described herein, showing suitable orientations of the various components described throughout. FIG. 9B shows an additional automated vitrification device as described herein, showing suitable orientations of the various components described throughout. FIG. 9C shows a photograph of an assembled automated vitrification device as described herein.

Exemplary materials for use in the various components of the automated vitrification devices described herein are well known in the art and include for example, various metals, plastics, polymers, ceramics and glasses. Methods for mechanically connecting the various components of the devices herein are also well known and readily implemented by one of ordinary skill in the art.

In additional embodiments, automated vitrification device 100 as shown in FIG. 1, FIGS. 9A, 9B and 9C, is provided. The device suitably comprises cryo-protectant holder 102, cryo-protectant dispenser 104 (suitably also comprising suction assembly 902 to provide suction for cryo-protectant dispenser 104, though the suction assembly can also be integrated into dispenser 104) and sample holder 208 oriented to allow a sample in the sample holder to be contacted with cryo-protectant from the cryo-protectant dispenser 104. The device suitably further comprises drying mechanism 106 for removing excess cryo-protectant from the sample, sample sealing device 110/108/112 comprising sealing mechanism 504 and a cutting mechanism 602/604 for first sealing the sample, then cutting the sealed sample 702. The device also comprises coolant holder 114 oriented to allow sealed sample 702 to be placed in a coolant in the coolant holder. Suitably, a control module is operably connected to cryo-protectant dispenser 104, sample holder 208 and sample sealing device 110/108/112. In embodiments, the various components of the device shown in FIG. 1, FIGS. 9A, 9B and 9C, are housed within chamber 116, the chamber comprising at least one opening for introduction of the sample to the sample holder 208.

As described herein, suitably cryo-protectant dispenser 104 is operably connected to a driving mechanism that controls the movement of cryo-protectant dispenser. Suitably, sample holder 208 is a rotating sample holder that moves about rotation point 210, so that the sample rotates or moves from a position that allows introduction of the sample, to a position that allows introduction of one or more cryo-protectants from cryo-protectant dispenser 104. Suitably, the rotating sample holder further moves the sample about rotation point 210 from the position that allows introduction of cryo-protectant to a position that allows sealing of the sample by sample sealing device 110/108/112. As described herein, suitably the sealing mechanism 504 comprises an adhesive film, and a cutting mechanism comprising first die 602 and second die 604 that align together so as to seal the sample and then cut the sealed sample.

Suitably, sealed sample 702 is released from the sample holder into coolant holder 114, suitably a coolant holder containing liquid nitrogen, for example, in one or more cryo-vials 802.

In further embodiments, containers for a biological sample are provided. The terms "containers for a biological sample," "sample holder" and "sample container" are used interchangeably throughout to refer to a device suitable for receiving a sample and allowing that sample to be manipulated for vitrification, e.g., allows for the introduction and removal of cryo-protectants, allows for sample sealing and vitrification, and allows for ultimate storage.

Figure 10:
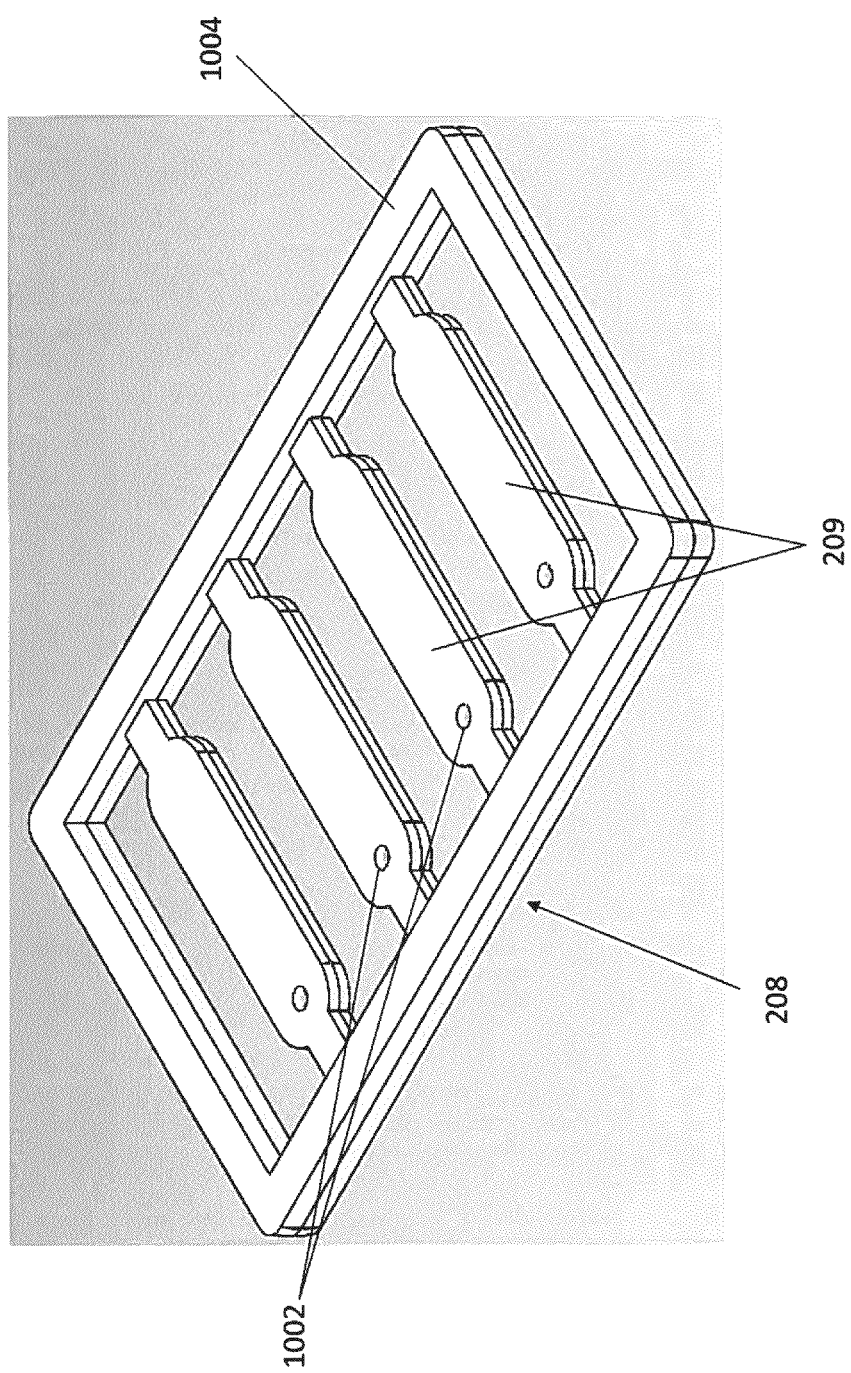
FIG. 10 shows an exemplary sample holder/container for a biological sample as described herein.

As shown in FIG. 10, an exemplary container for a biological sample 208 suitably comprises support member 209 having a top surface and a bottom surface. Container for a biological sample 208 also suitably comprises sample retention area 1002. Sample retention area 1002 suitably traverses support member 209 from the top surface to the bottom surface, thereby forming a hole passing through support member 209.

Sample retention area suitably comprises a porous mesh (not shown) positioned in the sample retention area. As used herein, "porous mesh" refers to any suitable material, i.e., cloth, polymer, plastic, metal, organic and synthetic sponges, etc. The porous mesh provides a surface for retention of the biological sample on the mesh, was also allowing for removal of a fluid, e.g., a cryo-protectant, from the mesh, by allowing the cryo-protectant to pass through the mesh. Suitably, sample retention area 1002 allows for introduction of a biological sample onto the porous mesh and removal of a fluid (e.g., cryo-protectant) from the porous mesh. Suitably, sample retention area 1002 is a substantially circular hole traversing support member 209.

Figure 11A:
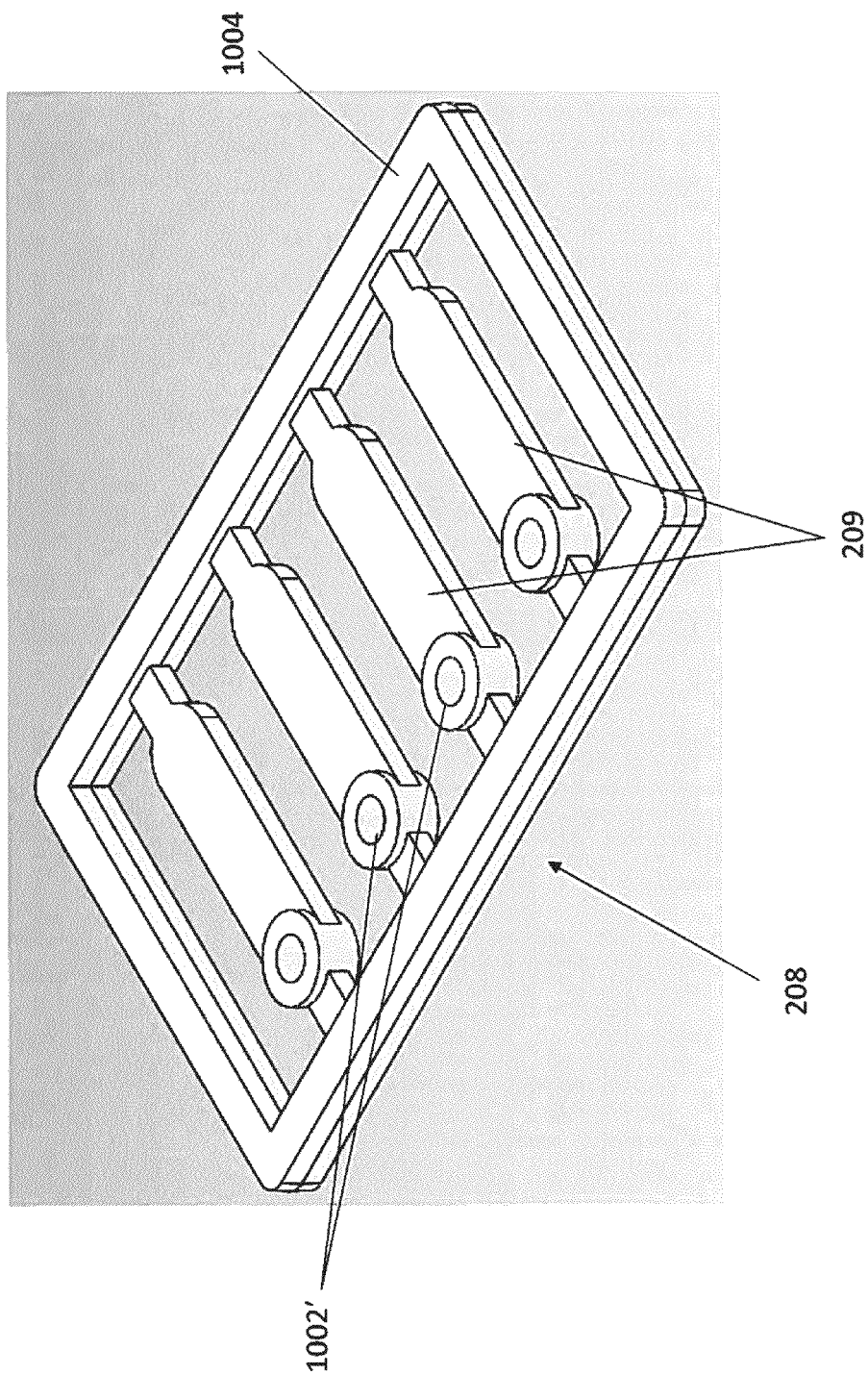
FIG. 11A shows an additional exemplary sample holder/container for a biological sample as described herein.

As shown in FIG. 11A, in exemplary embodiments, sample retention area 1002' can comprise an extension surrounding the hole, extending at least above the top surface of support member 209. This extension allows for the sample retention area to accommodate larger sample/cryo-protectant volumes as the increased height of the extension effectively provides a deeper retention area.

Figure 11B:
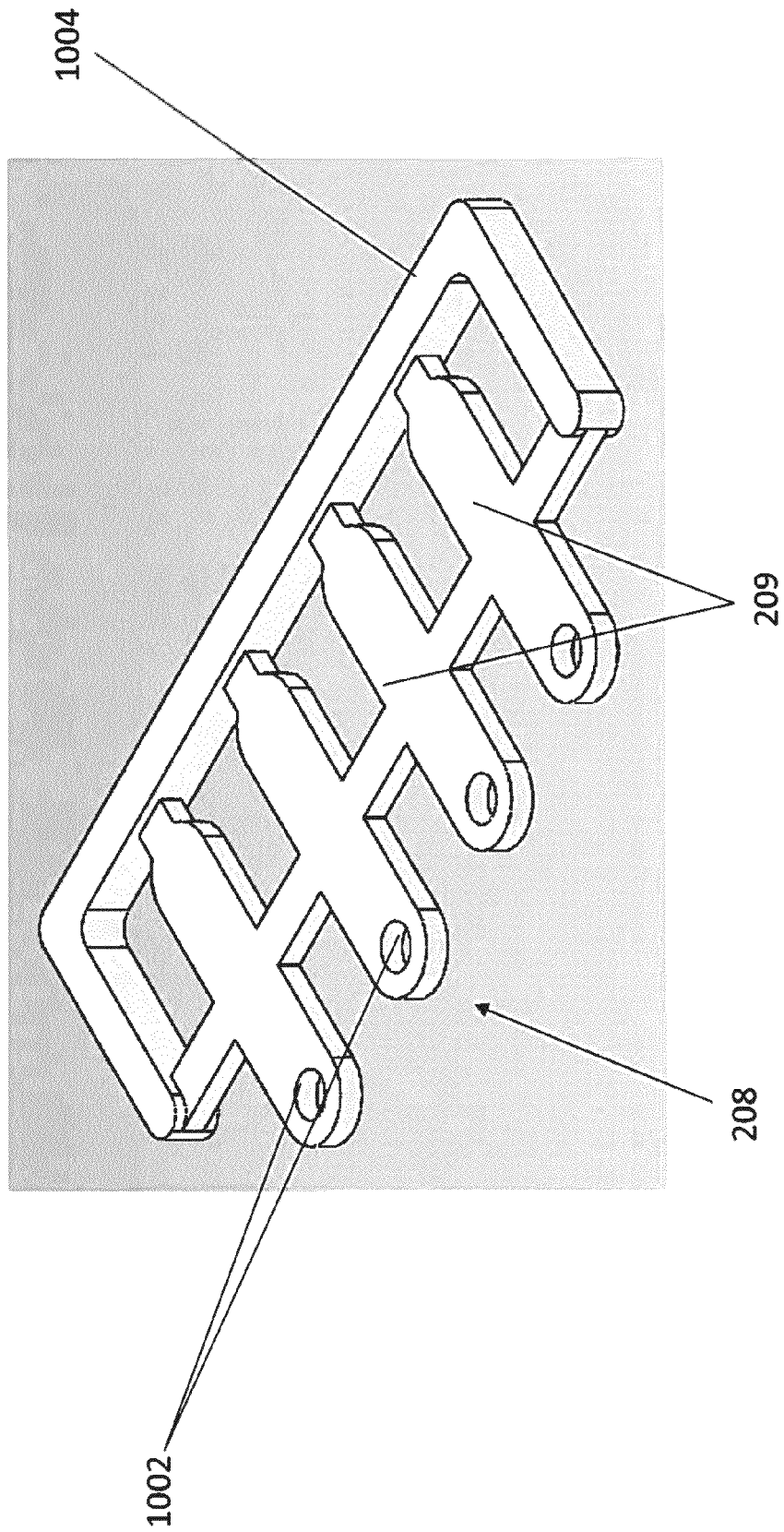
FIG. 11B shows an additional exemplary sample holder/container for a biological sample as described herein.

FIG. 11B shows a further container for a biological sample 208 as described herein.

As shown in FIGS. 10 and 11A-11B, container for a biological sample 208 suitably optionally comprises frame 1004 supporting container(s) 209. Use of frame 1004 allows for the preparation of a number of individual containers, each separate, but connected via a single frame surrounding the containers. In this way, multiple containers can be filled with samples, all of which are held together via frame 1004, for placement in the automated vitrification devices described throughout.

Exemplary materials for preparing the sample holders/containers described herein are well known in the art, and include for example various metals, plastics, polymers, ceramics, glasses, etc. Suitably, the containers are made from a two-part thermosetting plastic that starts as two liquids and hardens into a hard plastic. This method allows for casting a metal, plastic or cloth mesh in the sample retention area 1002. Additional methods for preparing the containers, include for example, injection molding.

In additional embodiments, sample handling apparatuses are provided. As shown in FIGS. 10 and 11A-11B, suitably such apparatuses comprise plurality of containers for a biological sample 208, each container comprising a support member 209 having a top surface and a bottom surface, a substantially circular hole traversing the support member from the top surface to the bottom surface (i.e., sample retention area 1002). Suitably, a porous mesh is positioned in the substantially circular hole. In exemplary embodiments, the substantially circular hole allows for introduction of a biological sample onto the porous mesh and removal of a fluid from the porous mesh. The plurality of containers 208 are suitably supported by frame 1004.

In exemplary embodiments the apparatus further comprises an extension surrounding the hole, extending at least above the top surface of support member 209.

In still further embodiments, methods of vitrifying a biological sample are provided. Suitably, such methods comprise placing a biological sample in sample holder 208 and placing a cryo-protectant in a cryo-protectant holder 102, suitably into reservoirs 206 of cryo-protectant holder 102. In exemplary embodiments, the placing of the biological sample in sample holder 208 comprises placing samples in each of the individual sample retention areas 1002 (e.g., holes) in the support members of a sample holder. Suitably, placing of the biological sample in the sample holder is carried out by a human operator, though it can be an automated process as well. In addition, placing the cryo-protectant (including multiple cryo-protectants) in the cryo-protectant holder is also suitably carried out by a human operator, though in further embodiments, this can also be an automated process.

The methods suitably further comprise dispensing the cryo-protectant from the cryo-protectant holder onto the sample. Suitably, this dispensing is carried out by cryo-protectant dispenser 104, for example, via a nozzle 304. The methods further comprise removing excess cryo-protectant from the sample via drying mechanism 106.

The methods suitably further comprise sealing and cutting the sealed sample. As described herein, suitably such sealing is carried out with the use of a sample sealing device 110/108/112 comprising sealing mechanism 504 and a cutting mechanism 602/604 for first sealing the sample, then cutting the sealed sample 702. Suitably, the sealing is carried out with adhesive film. In exemplary embodiments, the cutting comprises cutting the sealed sample with first die 602 and second die 604, that align together to cut the sealed sample.

Suitably, sealed sample 702 is then transferred into a coolant in a coolant holder 114, e.g., in a cryo-vial comprising liquid nitrogen, utilizing the various device components as described throughout.

As described herein, suitably the dispensing, removing, sealing, cutting and transferring that are carried out in the various methods described herein are automated via a control module, e.g., via a computer control or similar device.

Suitable computer control modules and programs for controlling and manipulating the various components of the devices as described herein are well known in the art and are readily determined and implemented by one of ordinary skill in the art.

In still further embodiments, the devices described herein can also be utilized for warming or thawing frozen biological samples (i.e., bringing biological samples to room temperature, or close to room temperature, so that they can be further utilized as desired), including for examples biological samples that have been vitrified utilizing the devices and methods described throughout. Thus, in embodiments the same device can be used to vitrify a biological sample and also warm or thaw the biological sample.

In embodiments, a sealed biological sample in a container for a biological sample as described herein is unsealed to expose the biological sample. Unsealing can be performed by an operator or can be an automated function of the devices described herein.

Following unsealing of the biological sample, the container with the biological sample is placed inside of the device, suitably on a sample holder as described herein. One or more warming solutions are then added to the biological sample. In embodiments, the warming solutions are held in the reservoirs of the cryo-protectant holder prior to being removed by cryo-protectant dispenser and then administered to the biological samples. The order, time and duration of administering the warming solutions to the biological samples is suitably controlled via a control module as described herein.

Suitably, the warming solutions are maintained at room temperature (e.g., about 20-30° C.) prior to administration to the biological samples, though if desired they can be warmed to higher temperatures. The warming solutions are utilized to slowly and safely raise the temperature of the biological samples to about room temperature prior to additional processing or use as desired.

Warming solutions suitably comprise sucrose, trehalose and SSS in mHTF. Suitable warming solutions comprise about 0.1 to about 1 M sucrose, about 0.05 to about 1 M trehalose and about 10% to about 30% SSS in mHTF. More suitably, warming solutions comprise about 0.2 to about 0.5 M sucrose, about 0.1 to about 0.5 M trehalose and about 15% to about 25% SSS in mHTF.

Exemplary warming solutions comprise 1) about 0.5 M sucrose, about 0.5 M trehalose and 20% SSS in mHTF; 2) about 0.3 M sucrose, about 0.3 M trehalose and about 20% SSS in mHTF; or 3) about 0.2 M sucrose, about 0.1 M trehalose and about 20% SSS in mHTF. In embodiments, such warming solutions are suitably used for warming of oocytes.

Additional exemplary warming solutions comprise 1) about 0.5 M sucrose, about 0.5 M trehalose and about 20% SSS in mHTF; 2) about 0.3 M sucrose, about 0.3 M trehalose and about 20% SSS in mHTF; or 3) about 0.2 M sucrose, about 0.1 M trehalose and about 20% SSS in mHTF. In embodiments, such warming solutions are suitably used for warming of blastocysts.

For example, in embodiments, cryo-protectant dispenser administers warming solutions to a biological sample in the amounts and for the durations indicated below. Drying mechanism 106 is suitably used to remove excess warming solution at the desired times/intervals prior to application of the next warming solution.

Described below is an exemplary warming solution protocol for warming/thawing of oocytes:
  A solution comprising about 0.5 M sucrose+about 0.5 M trehalose+about 20% SSS in mHTF is applied to the biological sample for about 1 minute at room temperature;
  Excess solution is removed;
  A solution comprising about 0.3 M sucrose+about 0.3 M trehalose+about 20% SSS in mHTF is applied to the biological sample for about 3 minutes at room temperature;
  Excess solution is removed
  A solution comprising about 0.2 M sucrose+about 0.1 M trehalose+about 20% SSS in mHTF is applied to the biological sample for about 3 minutes at room temperature;
  Excess solution is removed;
  A wash solution comprising about 20% SSS in mHTF is applied to the biological sample for about 3 minutes at room temperature;
  Excess solution is removed;
  The wash solution is applied again for about 3 minutes.

Described below is an exemplary warming solution protocol for warming/thawing of blastocysts:
  A solution comprising about 0.5 M sucrose+about 0.5 M trehalose+about 20% SSS in mHTF is applied to the biological sample for about 2-3 minutes at room temperature;
  Excess solution is removed;
  A solution comprising about 0.3 M sucrose+about 0.3 M trehalose+about 20% SSS in mHTF is applied to the biological sample for about 3 minutes at room temperature;
  Excess solution is removed;
  A solution comprising about 0.2 M sucrose+about 0.1 M trehalose+about 20% SSS in mHTF is applied to the biological sample for about 3 minutes at room temperature;
  Excess solution is removed;
  A wash solution comprising about 20% SSS in mHTF is applied to the biological sample for about 3 minutes at room temperature;
  Excess solution is removed;
  The wash solution is applied again for about 3 minutes.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

What is claimed is:

1. An automated vitrification device, comprising:
  a) a cryo-protectant holder;
  b) a cryo-protectant dispenser;
  c) a sample holder oriented to allow a sample in said sample holder to be contacted with cryo-protectant from said cryo-protectant dispenser;
  d) a sample sealing device;

e) a coolant holder oriented to allow a sealed sample to be placed in a coolant in said coolant holder; and f) a control module operably connected to said cryo-protectant dispenser, said sample holder and said sample sealing device.

2. The automated vitrification device of claim 1, wherein said cryo-protectant dispenser is operably connected to a driving mechanism that controls the movement of said cryo-protectant dispenser.

3. The automated vitrification device of claim 1, wherein a) through e) are housed within a chamber, said chamber comprising at least one opening for introduction of said sample to said sample holder.

4. The automated vitrification device of claim 1, wherein said sample holder is a rotating sample holder that moves said sample from a position that allows introduction of said sample, to a position that allows introduction of said cryo-protectant from said cryo-protectant dispenser.

5. The automated vitrification device of claim 4, wherein said rotating sample holder further moves said sample from said position that allows introduction of said cryo-protectant to a position that allows sealing of said sample by said sample sealing device.

6. The automated vitrification device of claim 1, wherein said coolant is liquid nitrogen.

7. The automated vitrification device of claim 1, further comprising a drying mechanism for removing excess cryo-protectant from said sample.

8. The automated vitrification device of claim 1, wherein said sample sealing device comprises a sealing mechanism and a cutting mechanism for first sealing said sample, then cutting said sealed sample, and then releasing said sealed sample from said sample holder into said coolant holder.

9. The automated vitrification device of claim 8, wherein said sealing mechanism comprises an adhesive film.

10. The automated vitrification device of claim 8, wherein said cutting mechanism comprises a first die and a second die that align together.

11. An automated vitrification device, comprising:
a) a cryo-protectant holder;
b) a cryo-protectant dispenser;
c) a sample holder oriented to allow a sample in said sample holder to be contacted with cryo-protectant from said cryo-protectant dispenser;
d) a drying mechanism for removing excess cryo-protectant from said sample;
e) a sample sealing device comprising a sealing mechanism and a cutting mechanism for first sealing said sample, then cutting said sealed sample;
f) a coolant holder oriented to allow said sealed sample to be placed in a coolant in said coolant holder; and
g) a control module operably connected to said cryo-protectant dispenser, said sample holder and said sample sealing device, wherein a) through f) are housed within a chamber, said chamber comprising at least one opening for introduction of said sample to said sample holder.

12. The automated vitrification device of claim 11, wherein said cryo-protectant dispenser is operably connected to a driving mechanism that controls the movement of said cryo-protectant dispenser.

13. The automated vitrification device of claim 11, wherein said sample holder is a rotating sample holder that moves said sample from a position that allows introduction of said sample, to a position that allows introduction of said cryo-protectant from said cryo-protectant dispenser.

14. The automated vitrification device of claim 13, wherein said rotating sample holder further moves said sample from said position that allows introduction of said cryo-protectant to a position that allows sealing of said sample by said sample sealing device.

15. The automated vitrification device of claim 11, wherein said coolant is liquid nitrogen.

16. The automated vitrification device of claim 11, wherein said sample sealing device further allows releasing said sealed sample from said sample holder into said coolant holder.

17. The automated vitrification device of claim 11, wherein said sealing mechanism comprises an adhesive film.

18. The automated vitrification device of claim 11, wherein said cutting mechanism comprises a first die and a second die that align together.

* * * * *